United States Patent [19]

Goudie

[11] 3,963,750

[45] June 15, 1976

[54] THIOPHENE DERIVATIVES

[75] Inventor: Alexander Crossan Goudie, Harlow, England

[73] Assignee: Beecham Group Limited, Great Britain

[22] Filed: July 23, 1974

[21] Appl. No.: 491,060

[30] Foreign Application Priority Data

Aug. 9, 1973  United Kingdom............... 37699/73

[52] U.S. Cl.......................... 260/332.2 C; 424/275; 260/329 AM; 260/332 S
[51] Int. Cl.².................................... C07D 333/24
[58] Field of Search ............................. 260/332.2 C

[56] References Cited
UNITED STATES PATENTS 3,832,354  8/1974  Gadient et al. .............. 260/332.2 C

OTHER PUBLICATIONS

Gewald et al., "Chemical Abstracts," vol. 64, (1966), p. 8118.

Primary Examiner—James O. Thomas, Jr.
Assistant Examiner—A. Sigel

[57] ABSTRACT

Compounds of the formula:

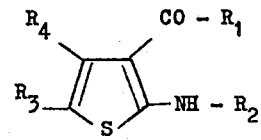

wherein $R_1$ is $NHR_5$ or $OR_5$ where $R_5$ is a hydrogen atom or alkyl group of 1–6 carbon atoms; $R_2$ is a hydrogen atom or a $CO.R_6$ group where $R_6$ is an alkyl group of 1–6 carbon atoms; $R_3$ is a phenyl group substituted by 1 or 2 halogen atoms or methyl, trifluoromethyl or methoxyl groups; and $R_4$ is a hydrogen atom or an alkyl group of 1–6 carbon atoms or a phenyl group optionally substituted by 1 or 2 halogen atoms or methyl, trifluoromethyl or methoxyl groups; and salts thereof; have been found to possess valuable antiinflammatory properties. The preparation and use of such compounds is described.

4 Claims, No Drawings

THIOPHENE DERIVATIVES

The present invention relates to derivatives of 2-amino-3-carboxythiophene, to a process for their manufacture and to pharmaceutical compositions containing them which are useful in the treatment of inflammatory conditions such as arthritis.

The present invention provides compounds of the formula (I):

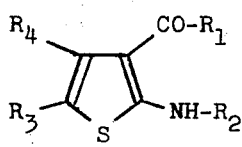

wherein $R_1$ is $NHR_5$ or $OR_5$ where $R_5$ is a hydrogen atom or a lower alkyl group; $R_2$ is a hydrogen atom or a $CO.R_6$ group where $R_6$ is a lower alkyl group; one of the groups $R_3$ or $R_4$ is a substituted phenyl group and the other group $R_3$ or $R_4$ is a hydrogen atom or a lower alkyl or optionally substituted phenyl group; and salts thereof if $COR_1$ is an acid group.

When used herein, the term "lower alkyl" means an alkyl group of 1 – 6 carbon atoms. When used herein, the term "substituted phenyl" means the phenyl group substituted by 1 or 2 halogen atoms or methyl, trifluoromethyl or methoxyl groups.

Preferably $R_2$ is a hydrogen atom.

Suitable groups $R_5$ include the hydrogen atom and the methyl, ethyl, n-propyl, iso-propyl, butyl, pentyl and hexyl groups.

Preferred groups $R_5$ include the hydrogen atom and the methyl and ethyl groups.

Suitable groups $R_6$ include the methyl, ethyl and propyl groups.

The preferred group $R_6$ are the methyl and ethyl groups.

Preferred groups $R_4$ include the hydrogen atom and the methyl, ethyl and phenyl groups, the hydrogen atom being particularly preferred.

One particularly suitable sub-group of compounds within formula (I) are those of formula (II):

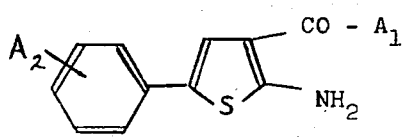

wherein $A_1$ is a group of the formula $OA_3$ or $NHA_3$, where $A_3$ is a hydrogen atom or a lower alkyl group; and $A_2$ is a halogen atom or a methyl, trifluoromethyl or methoxyl group.

Most suitably $A_2$ is a fluorine, chlorine or bromine atom or a trifluoromethyl group.

Preferably $A_2$ is a 4-fluorine atom.

Most suitably $A_1$ is an amino, methylamino, methoxyl or ethoxyl group.

Preferably $A_1$ is an amino group.

When the compound of the formula (I) is a carboxylic acid it may be in the form of an alkali metal salt, alkaline earth metal salt, ammonium or substituted ammonium salt or other conventional salt. Preferred salts include the sodium and potassium salts.

The compounds of formula (I) wherein $R_2$ is a hydrogen atom may be prepared by the reaction of sulphur and compounds of the formulae (III) and (IV):

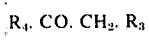

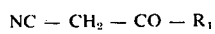

wherein $R_1$, $R_3$ and $R_4$ are as defined in relation to formula (I). The compounds wherein $R_1$ is OH are more suitably prepared by the hydrolysis of a corresponding amide or ester.

This condensation reaction is similar to that described by K. GEWALD, E. SCHINKE and H. BOETTEHER in Chem. Ber., 99, 94 — 100 (1966).

Normally the reaction is carried out in an organic solvent such as dimethylformamide or similar inert solvent at non-extreme temperatures. Generally, the reaction temperatures are ambient or slightly elevated, for example, 15° – 100°C, preferably 30° – 80°C.

The condensation reaction is normally carried out in the presence of a base, such as diethylamine, morpholine or triethylamine.

Compounds of the formula (I) wherein $R_2$ is a $COR_6$ group may be prepared from the corresponding amino compound by conventional methods of acylation such as by reaction with an acid anhydride, or more suitably an acid halide, using for example, pyridine as a solvent.

The compounds of this invention possess useful anti-inflammatory activity. Accordingly, in a further aspect, the invention provides a pharmaceutical composition comprising a compound of the formula (I) as hereinbefore defined, together with a pharmaceutically acceptable carrier. Most suitably the compound of formula (I) included in the composition is one of formula (II) as hereinbefore defined.

The compositions of this invention may be in the form of conventional oral or parenteral unit doseage forms such as, for example, tablets, capsules, sachets, suppositories, injectables and the like. For convenience in administration, oral forms such as tablets, capsules and the like are preferred. Unit doseforms will normally contain from 6–600mgs. of active compound, preferably 10–300mgs, for example, 20–200mgs. The following examples illustrate the invention:

Example 1

2-Amino-5-(4-fluorophenyl)-3-thiophene carboxamide

To a stirred mixture of cyanoacetamide (0.1 mole), sulphur (0.1 mole) and diethylformamide (20 ml) at 40°–45° was added triethylamine (7.5 ml). The resulting dark brown solution was treated dropwise over 1½ hours, with 4-fluorophenyl-acetaldehyde (0.1 mole) while the reaction mixture was maintained at 40°–45°. After the solution had been stirred at room temperature for 16 hours, it was cooled (ice bath) and poured on to water (60 ml) at 5°C. The precipitate was collected by filtration, washed with water and dried. Recrystallisation from propanol yielded 2-amino-5-(4-fluorophenyl)-3-thiophenecarboxamide (40%, m.p. 227°–30°).

The following compounds were prepared in a similar manner to Example 1 and had the following melting points:

2-Amino-5-(2-fluorophenyl)-3-thiophene carboxamide, m.p. 170°–1° (aqueous ethanol).

2-Amino-5-(4-methylphenyl)-3-thiophene carboxamide, m.p. 228°–30° (ethanol).
2-Amino-5-(4-chlorophenyl)-3-thiophene carboxamide, m.p. 255°–7° (ethanol).
2-Amino-5-(3-chlorophenyl)-3-thiophene carboxamide, m.p. 190°–2° (ethanol).

Example 2

2-Acetamido-5-(4-fluorophenyl)-3-thiophenecarboxamide.

A vigorously stirred mixture of 2-amino-5-(4-fluorophenyl)-3-thiophenecarboxamide (0.01 mole) and pyridine (20 ml) at 0° was treated dropwise with acetyl chloride (0.011 mole). The resulting solution was stirred a further 30 minutes at 0° and then poured on to cold water. The precipitate was collected by filtration, washed with water and dried. Recrystallisation from ethanol yielded 2-acetamido-5-(4-fluorophenyl)-3-thiophenecarboxamide (90%, m.p. 230°–3°).

Example 3

2-Amino-5-(4-fluorophenyl)-3-thiophene N-methylcarboxamide

As example 1, except that N-methylcyanoacetamide replaced cyanoacetamide. The precipitate was recrystallised from aqueous ethanol to afford 2-amino-5-(4-fluorophenyl)-3-thiophene N-methyl carboxamide in 40% yield, m.p. 168° (decomp.)

Example 4

Ethyl 2-amino-5-(4-fluorophenyl)-3-thiophene carboxylate.

As example 1, except that ethyl cyanoacetate replaced cyanoacetamide. Recrystallisation of the crude product from hexane afforded ethyl 2-amino-5-(4-fluorophenyl)-3-thiophene carboxylate, m.p. 98°–9°.

In a similar manner was prepared ethyl 2-amino-5-(3-chlorophenyl)-3-thiophene carboxylate, m.p. 110°–11° (hexane).

Example 5

2-Amino-5-(4-fluorophenyl)-3-thiophene carboxylic acid.

A mixture of ethyl 2-amino-5-(4-fluorophenyl)-3-thiophene carboxylate (2g), sodium hydroxide (1g) and ethanol (20 ml) was refluxed for 5 hours, cooled and then concentrated. The solid residue was dissolved in water, filtered and acidified at 0°C. The light brown precipitate was collected by filtration to give pure 2-amino-5-(4-fluorophenyl)-3-thiophene carboxylic acid, m.p. 172°–4°.

Example 6

2-Amino-4-(4-chlorophenyl)-3-thiophene carboxamide.

A mixture of 4-chloroacetophenone (100g), cyanoacetamide (54.5g), ammonium acetate (10g), glacial acetic acid (32g) and benzene (130 ml) was refluxed overnight with constant removal of water.

From the cooled solution was obtained pure 1-(4-chlorophenyl)-ethylidene cyanoacetamide, m.p. 165°–7°.

A mixture of 1-(4-chlorophenyl)-ethylidene cyanoacetamide (37.4g), sulphur (5.43g), diethylamine (17 ml) and ethanol (70 ml) was stirred at 50°–60° for 3 hours, cooled and added to water (200 ml). Recrystallisation of the crude product from benzene gave pure 2-amino-4-(4-chlorophenyl)-3-thiophene carboxamide, m.p. 159°–60°.

In a similar manner was prepared 2-amino-4-(4-fluorophenyl)-3-thiophene carboxamide, m.p. 150°–1° (ethyl acetate/hexane).

Example 7

2-Amino-5-(4-fluorophenyl)-4-phenyl-3-thiophene carboxamide.

A mixture of 4-fluorobenzyl phenyl ketone (50g), morpholine (45g) and benzene (100ml) was refluxed overnight with molecular sieve, type 4A, to afford 2-(4-fluorophenyl)-1-phenyl-1-morpholinoethylene. The latter compound (0.2 mole), cyanoacetamide (0.2 mole), diethylamine (2ml), sulphur (0.2 mole) and ethanol (100 ml) were stirred overnight at room temperature and then added to water. The crude product was recrystallised from ethanol and then from nitromethane to give pure 2-amino-5-(4-fluorophenyl)-4-phenyl-3-thiophene carboxamide, m.p. 205°–7°.

What we claim is:
1. A compound of the formula (II):

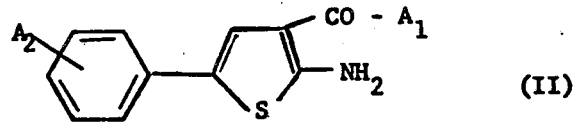

(II)

or a pharmaceutically acceptable non-toxic salt thereof, wherein $A_1$ is $NHA_3$ wherein $A_3$ is hydrogen or alkyl of 1–6 carbon atoms; and $A_2$ is fluorine.

2. A compound according to claim 1 wherein $A_2$ is 4-fluorine.

3. A compound according to claim 2 wherein $A_1$ is amino or methylamine.

4. 2-Amino-5-(4-fluorophenyl)-3-thiophenecarboxamide.